United States Patent [19]

Ramin et al.

[11] Patent Number: 5,683,681

[45] Date of Patent: Nov. 4, 1997

[54] COSMETIC COMPOSITIONS FOR APPLICATION TO THE NAIL

[75] Inventors: Roland Ramin, Itteville; Jean Mondet, Aulnay Sous Bois, both of France

[73] Assignee: L'Oreal, Paris, France

[21] Appl. No.: 417,674

[22] Filed: Apr. 6, 1995

[30] Foreign Application Priority Data

Apr. 7, 1994 [FR] France .................. 94 04114

[51] Int. Cl.⁶ .................................................. A61K 7/04
[52] U.S. Cl. .................................. 424/61; 424/401
[58] Field of Search ............ 424/61, 401; 514/951; 524/501

[56] References Cited

U.S. PATENT DOCUMENTS 4,254,003  3/1981  Fox et al. .................. 260/29.6
4,957,730  9/1990  Bohn et al. ................. 424/61
5,093,108  3/1992  Pappas et al. .............. 424/61
5,264,206  11/1993 Bohn et al. ................. 424/61

FOREIGN PATENT DOCUMENTS 1154-347-A  9/1983   Canada .
A-0226984   7/1987   European Pat. Off. .
A-0298271   1/1989   European Pat. Off. .
A-2397186   2/1979   France .
1032367     6/1966   United Kingdom .
2002795     2/1979   United Kingdom .

*Primary Examiner*—Thurman K. Page
*Assistant Examiner*—Sharon Howard
*Attorney, Agent, or Firm*—Finnegan, Henderson, Farabow, Garrett & Dunner, L.L.P.

[57] ABSTRACT

A cosmetic composition for application to the nail, comprising an aqueous dispersion of polymers and a plasticizer. The composition may be used as a varnish or a base layer for a traditional varnish, and/or as a treatment base for the nail.

14 Claims, No Drawings

COSMETIC COMPOSITIONS FOR APPLICATION TO THE NAIL

The present invention is directed to a cosmetic composition for application to the nails, which comprises an aqueous dispersion of at least one film-forming polymer.

Some aqueous dispersions of particular polymers are known to display advantageous film-forming properties. This is especially known in the field of make-up and/or treatment products for the nails, as is shown, for example, in Patent Applications JP 4103514, EP 143480 or EP 418469, the disclosures of which are incorporated herein by reference, which describe the use of an aqueous dispersion of polymer as a nail varnish or a nail varnish base. Depending on the case, these varnishes may be removed by peeling or using an organic solvent, which can give rise to an adverse change in the outer surface of the nail. This adverse change is of mechanical origin in the case of peeling, and is of chemical origin in the case of the use of a solvent.

Furthermore, when it is desired to treat the nail, for example using a protective or hardening agent, the removing of the base containing this agent with a make-up remover containing an organic solvent can decrease the advantages obtained by the treatment.

The inventor set himself to the task of remedying the drawbacks of the prior art, and of providing a cosmetic composition capable of being applied to the nail and which could be removed otherwise than by using an organic solvent.

Surprisingly, it was found that, if an appropriate aqueous dispersion was chosen, in combination with an appropriate plasticizer, a composition was obtained which, while retaining excellent film-forming properties at room temperature, could be removed by simply washing with water.

A subject of the present invention is thus a cosmetic composition for application to the nail, comprising an aqueous dispersion of particles of at least one film-forming, radical-polymerization polymer and at least one plasticizer, wherein the at least one film-forming polymer contains carboxylic acid functions that are partially neutralized so that the film-forming polymers are water insoluble but are soluble in an organic solvent. Preferably, the carboxylic acid functions of the at least one film-forming polymer are neutralized by means of a monobasic neutralizing agent and have a degree of neutralization which preferably ranges from 10 to 80%.

Hence the cosmetic composition according to the invention has the advantage of being readily applicable to the entire surface of the nail and of being readily and completely removable by simply washing the hands with water, without having to use a make-up remover, or even hot water and/or strongly soapy water.

Furthermore, since the cosmetic composition according to the invention has water as its solvent, it is possible to introduce active agents, most of which are water-soluble, into it, for example so as to protect, harden and/or treat the nail.

An aqueous nail treatment varnish is thereby obtained, which, though applied in a single layer, takes the form of a sufficiently thick film to be able to perform its functions, namely to isolate properly the active agents deposited on the nail from the outside.

Lastly, the use of a polymer in dispersion enables a composition of appropriate viscosity to be obtained, which is not the case if a water-soluble polymer is used, with which polymer the viscosity of the solution obtained, for a concentration of 25%, is too great to permit correct application to the nail.

In the present description below, the percentages are given by weight except where otherwise stated.

The aqueous dispersion according to the invention is prepared according to a standard process for preparing such dispersions.

This standard process consists in dissolving a water-insoluble polymer in an organic solvent, in mixing the solution thereby obtained with water so as to form an emulsion, and then in removing the organic solvent by evaporation under reduced pressure so as to obtain an aqueous dispersion consisting of particles of the polymer whose size is generally less than one μm.

According to the present invention, the film-forming polymers in question containing carboxylic acid functions are synthetic polymers preferably having an average molecular weight ranging from 5,000 to 700,000.

Among these film-forming polymers, the following may be mentioned in particular:

polyoxyethylenated vinyl acetate/crotonic acid copolymers;

vinyl acetate/crotonic acid (90:10) copolymer;

vinyl acetate/crotonic acid/vinyl neodecanoate terpolymers;

N-octylacrylamide/methylmethacrylate/hydroxypropyl methacrylate/acrylic acid/tertbutylaminoethyl methacrylate copolymers;

methyl vinyl ether/maleic anhydride (50:50) alternating copolymer monoesterified with butanol;

acrylic acid/ethyl acrylate/N-tertbutylacrylamide terpolymers; and polymers corresponding to the following formula:

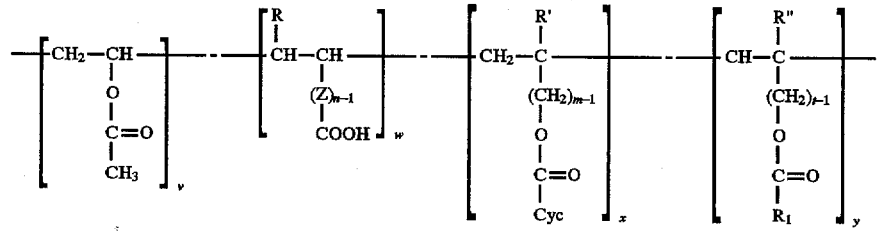

in which:

R, R' and R", which may be identical or different, represent a hydrogen atom or a methyl radical;

m, n and t are equal to 1 or 2;

$R_1$ represents a saturated or unsaturated, linear or branched alkyl radical having from 2 to 21 carbon atoms;

Z represents a bivalent radical selected from the group consisting of:

—$CH_2$—, —$CH_2$—O—$CH_2$— and —$CH_2$—O—$(CH_2)_2$—;

Cyc represents a radical selected from

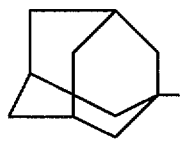

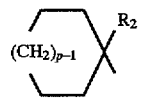

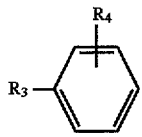

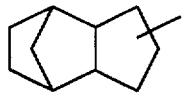

in which $R_2$ represents a hydrogen atom or a methyl radical;

$R_3$ represents a hydrogen atom or a methyl, ethyl, tert-butyl, ethoxy, butoxy or dodecyloxy radical;

$R_4$ represents a hydrogen atom, an alkyl radical having from 1 to 4 carbon atoms or an alkoxy radical having from 1 to 4 carbon atoms;

p is equal to 1 or 2;

v represents from 10 to 91%, and preferably from 36 to 84%, by weight;

w represents from 3 to 20%, and preferably from 6 to 12%, by weight;

x represents from 4 to 60%, and preferably from 6 to 40%, by weight;

y represents from 0 to 40%, and preferably from 4 to 30%, by weight;

v+w+x+y being equal to 100%.

The organic solvent used is preferably a volatile solvent or a mixture of such solvents having a boiling point below that of water, in other words, the solvent used must be more volatile than water in order to ensure that the solvent is evaporated before the water. Thus, solvents that are volatile at ambient temperature are preferred. The solvent used must also be miscible or partially miscible with water.

Acetone, methyl ethyl ketone, tetrahydrofuran, methyl acetate, ethyl acetate, isopropanol and/or ethanol may, for example, preferably be used as a solvent.

During the preparation of the aqueous dispersions which are usable in the compositions according to the invention, the carboxylic acid functions of the film-forming polymers are at least partially neutralized.

This neutralization may be carried out by adding a neutralizing agent to the solution of the polymer in the organic solvent, before formation of the emulsion. It may also be carried out directly, during the formation of the emulsion, by adding the neutralizing agent to the aqueous phase.

The degree of neutralization of the film-forming polymers containing carboxylic acid functions must be determined in such a way that they remain water-insoluble while being soluble in the organic solvent. Thus, this degree of neutralization must be less than 100%.

The lower and upper limiting degrees of neutralization which should not be exceeded in order for the polymer to remain water-insoluble are dependent on the nature of each polymer and can be easily determined by a person skilled in the art on the basis of his general technical knowledge.

Generally speaking, the degree of neutralization ranges from 30 to 80% if the polymer has less than 2 meq/g of carboxylic acid functions, and ranges from 10 to 50% if the polymer has more than 2 meq/g of carboxylic acid functions.

The neutralization of the carboxylic acid functions is carried out using a non-volatile monobasic compound such as an inorganic base, for instance, sodium hydroxide or potassium hydroxide, or an amino alcohol taken, for example, from the group consisting of 2-amino-2-methyl-1-propanol (AMP), triethanolamine, triisopropanolamine (TIPA), monoethanolamine, diethanolamine, tris(2-hydroxy-1-propyl)amine, 2-amino-2-methyl-1,3-propanediol (AMPD) and 2-amino-2-hydroxymethyl-1,3-propanediol.

After partial neutralization of the polymer, an emulsion is prepared by pouring a suitable amount of water, optionally containing an anti-foaming agent enabling the subsequent evaporation of the organic solvent to be facilitated, with stirring into the organic solution obtained.

The emulsion thereby obtained is especially stable without it being necessary to employ a surfactant, inasmuch as the carboxylate groups of the polymer position themselves at the interface with water and protect the droplets against coalescence by electrostatic repulsion.

After formation of the emulsion, preferably at a temperature ranging from room temperature to approximately 70° C., the evaporation of the organic solvent is then performed under reduced pressure until it has been removed completely, the evaporation preferably being carried out with gentle heating.

An aqueous dispersion of particles of the film-forming polymer is thereby obtained, which dispersion is free from any surfactant or other hydrophilic stabilizer while being very stable.

The average size of the particles ranges from 10 to 300 nm, but is preferably less than 250 nm, with a relatively small size polydispersity of the particles which preferably ranges from 0.1 to 0.4, and more preferably ranges from 0.1 to less than 0.35.

In order to obtain an aqueous dispersion which is useable in a cosmetic composition according to the invention, at least one plasticizer is introduced into the cosmetic composition.

This plasticizer can be hydrophilic or hydrophobic. It is chosen so as to make possible, in combination with the polymer in question, a film which can be completely removed with water by simply washing the hands.

It is also chosen so as to make possible, after application of the dispersion and drying of the film, the obtaining of a film of surface energy 30–55 mJ/m² and of polarity 0 to 0.34, preferably less than 0.25.

The plasticizer may be introduced, mixed in the organic solvent, during the preparation of the aqueous dispersion, in particular when it is of the hydrophobic type. When it is of the hydrophilic type, it may be introduced directly into the dispersion after its formation.

Among plasticizers which can be used in the present invention, the following may be preferably mentioned:

Carbitols of the company Union Carbide, namely Carbitol or diethylene glycol ethyl ether, Methyl Carbitol or diethylene glycol methyl ether, Butyl Carbitol or diethylene glycol butyl ether or alternatively Hexyl Carbitol or diethylene glycol hexyl ether, Cellosolves of the company Union Carbide, namely Cellosolve or ethylene glycol ethyl ether, Butyl Cellosolve or ethylene glycol butyl ether or Hexyl Cellosolve or ethylene glycol hexyl ether, propyl glycol derivatives, and especially propylene glycol phenyl ether, propylene glycol diacetate, dipropylene glycol butyl ether, tripropylene glycol butyl ether and also Dowanols of the company Dow Chemical, such as Dowanol PM or propylene glycol methyl ether, Dowanol DPM or dipropylene glycol ethyl ether, Dowanol TPM or tripropylene glycol methyl ether and Dowanol DM or diethylene glycol methyl ether, benzyl alcohol, triethyl citrate, 1,3-butylene glycol, diethyl, dibutyl and diisopropyl phthalates and adipates, diethyl and dibutyl tartrates, diethyl, dibutyl and di(2-ethylhexyl) phosphates, and glycerol esters such as glyceryl diacetate (diacetin) and glyceryl triacetate (triacetin).

Preferably, from 5 to 40% of plasticizer are introduced relative to the weight of dry matter of neutralized film-forming polymer, the plasticizer being distributed according to its partition coefficient between the particles and the aqueous phase.

An aqueous dispersion according to the invention, in which the weight concentration of the film-forming polymer in the form of particles in dispersion preferably ranges from 5 to 50% relative to the total weight of the dispersion, is thereby obtained.

The viscosity of the dispersion, at a concentration of 25%, is preferably between 10 and 3,000 mPa.s (measured at 25° C.).

The cosmetic compositions according to the invention are readily removed by simply washing the hands with water.

The cosmetic composition according to the invention may be used as a base layer for a traditional solvent-containing nail varnish or, where appropriate, as a readily removable varnish.

When the compositions according to the invention are used as a base layer for a solvent varnish, it is found that the nail has no tendency to become tinted on subsequent application of the solvent-containing varnish, as is the case in the state of the art; this being due to the fact that the nail is not in direct contact with the varnish. When pigments are introduced into the compositions, they may be used as varnish.

Lastly, it is also possible to introduce into these cosmetic compositions, in solution or dispersion, active agents such as agents for protecting, hardening and/or treating the nail, so as to obtain a treatment base for the nail, which can be subsequently covered with traditional varnish.

In the particular mode of use as a nail treatment, it is possible to conceive of applying the base containing the active agents to the nail at night, enabling the nail to be treated during the night, and then a removal of this base in the morning by simply washing the hands.

Among useable active agents, there may be mentioned vitamins and their derivatives, raw materials of biological origin and their derivatives, such as keratin, proteins, hydrolysates, chitosan, melanin, trace elements and collagen, glycerol, phospholipids, urea and formal.

The invention is illustrated in greater detail in the examples which follow.

EXAMPLE 1

Preparation of an aqueous dispersion of vinyl acetate/crotonic acid/vinyl 4-tertbutylbenzoate (65:10:25) copolymer The preparation of this copolymer is described in Example 19 of French Patent No. 78/30596 (FR 2,439,798), the disclosure of which is incorporated herein by reference, and enables a copolymer which takes the form of beads 0.5 to 1 mm in diameter to be obtained.

100 g of the copolymer defined above (acid value: 65) were added with stirring to a solution containing 275 g of acetone and 25 g of diisopropyl adipate.

After stirring at room temperature for 30 minutes, dissolution of the copolymer was complete.

To the organic phase thereby obtained, an aqueous phase was added over approximately 5 minutes, at room temperature and with stirring by means of a shearing disperser of the Ultra-Turrax type at 2000 rpm, in order to produce the emulsion.

The aqueous phase consisted of 260.55 g of deionized water, 1.14 g of a silicone antifoam and 6.21 g of 2-amino-2-methyl-1-propanol (amount corresponding to 60% neutralization on the basis of the acid value).

Stirring was continued for 10 to 15 min, the outcome of which was that a translucent and stable emulsion was obtained.

The emulsion was then concentrated using a rotary evaporator under a partial vacuum at a temperature below 45° C.

After complete removal of the acetone, a stable milky dispersion of low viscosity was obtained, which displayed the following features:

concentration of the polymer in the dispersion: 25% particle size: 58 nm (measured by quasi-elastic light scattering using a Coulter model M4)

polydispersity: 0.3 film surface energy: 50 mJ/m$^2$ polarity: 0.24

EXAMPLE 2

Preparation of an aqueous dispersion of vinyl acetate/crotonic acid/vinyl neodecanoate copolymer (resin 28-2930, National Starch)

60 g of the copolymer defined above (acid value: 65) were added with stirring to a solution containing 231 g of methyl ethyl ketone, 3 g of 2-amino-2-methyl-1-propanol (amount corresponding to 50% neutralization on the basis of the acid value) and 12 g of diisopropyl adipate.

After stirring at room temperature for 30 minutes, dissolution of the copolymer was complete.

To the organic phase thereby obtained, an aqueous phase was added at 60° C. and with stirring by means of a shearing disperser of the Ultra-Turrax type at 2000 rpm, in order to produce the emulsion, said aqueous phase consisting of 331 g of deionized water and 0.69 g of a silicone antifoam.

Stirring was continued for 10 to 15 min, the outcome of which was that a translucent and stable emulsion was obtained.

The emulsion was then concentrated using a rotary evaporator under a partial vacuum at a temperature below 45° C.

After complete removal of the acetone, a stable milky dispersion of low viscosity was obtained, displaying the following features:

concentration of the polymer in the dispersion: 15% particle size: 200 nm (measured by quasi-elastic light scattering using a Coulter model M4)

polydispersity: 0.28 film surface energy: 30 mJ/m$^2$ polarity: 0

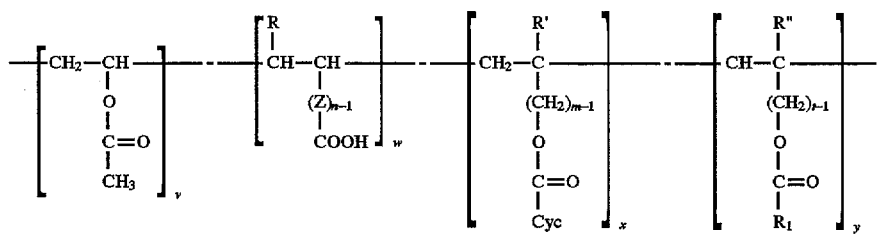

EXAMPLE 3

Nail treatment

The following composition was prepared by simply mixing the constituents and stirring:

| | |
|---|---:|
| aqueous dispersion of Example 1 | 96.8985 g |
| glycerol | 3 g |
| magnesium glutamate | 0.0005 g |
| copper glutamate | 0.0005 g |
| manganese glutamate | 0.0005 g |
| soya bean protein | 0.1 g |

This composition was readily applicable to the nail and dried in approximately 5–10 minutes. A glossy film was thereby obtained, which was readily removed with water and hence enabled the use of an organic solvent to be avoided.

Daily application of this composition to the nail should enable the general appearance of the nail to be improved.

EXAMPLE 4

Nail Treatment

The following composition was prepared by mixing the aqueous dispersion, glycerol and formaldehyde, followed by gentle stirring and then by dispersing the hydroxypropylcellulose in the solution obtained.

| | |
|---|---:|
| aqueous dispersion according to Example 2 | 82.3 g |
| water | 15 g |
| glycerol | 2 g |
| formaldehyde | 0.5 g |
| hydroxypropylcellulose | 0.2 g |

A composition was obtained which was readily applicable to the nail and which gave, after drying, a glossy film which was readily removed with water.

Daily application of this composition to the nail makes it possible, after several weeks of application, to obtain a resultant hardening of soft nails.

What is claimed is:

1. A cosmetic composition for application to the nail, comprising an aqueous dispersion of particles of at least one film-forming, radical-polymerization polymer and at least one plasticizer, wherein said at least one film-forming polymer contains carboxylic acid functions partially neutralized so that said at least one film-forming polymer is water insoluble but is soluble in an organic solvent.

2. A composition according to claim 1, wherein in said polymers corresponding to the formula v represents from 36 to 84% by weight, w represents from 6 to 12% by weight, x represents from 6 to 40% by weight, y represents from 4 to 30% by weight, and v+w+x+y being equal to 100%.

3. A composition according to claim 1, wherein said at least one plasticizer is present in a proportion ranging from 5 to 40% by weight relative to the weight of dry matter of neutralized film-forming polymer.

4. A composition according to claim 1, wherein said aqueous dispersion additionally contains at least one active agent, said active agent being a vitamin keratin, a protein, a hydrolysate, chitosan, melanin, a trace element, collagen, glycerol, a phospholipid urea or formal.

5. A composition according to claim 1, wherein said aqueous dispersion additionally contains pigments.

6. A composition according to claim 1, which enables obtaining a film, after drying, with surface energy 30–55 mJ/m$^2$ and with polarity 0–0.34.

7. A composition according to claim 1, wherein said particles of said aqueous dispersion range in average size from 10 to 300 nm.

8. A composition according to claim 7, wherein said particles have an average size from 10 to less than 250 nm.

9. A composition according to claim 1, wherein the weight concentration of the film-forming polymer in the form of particles in dispersion ranges from 5 to 50% relative to the total weight of the dispersion.

10. A method for the treatment of the nails, which comprises applying a composition according to claim 1 to the nails, wherein said composition further comprises at least one active treatment agent.

11. A composition according to claim 1, wherein said at least one film forming polymer contains carboxylic acid functions neutralized by a monobasic neutralizing agent and further wherein said at least one film-forming polymer has a degree of neutralization ranging from 10 to 80%.

12. A composition according to claim 7, wherein said particles have a polydisperity ranging from 0.1 to 0.4.

13. A composition according to claim 12, wherein said particles have a polydisperity ranging from 0.1 to less than 0.35.

14. A cosmetic composition for application to the nail, comprising an aqueous dispersion of particles of at least one film-forming, radical-polymerization polymer and at least one plasticizer, wherein said at least one film-forming polymer contains carboxylic acid functions partially neutralized so that said at least one film-forming polymer is water insoluble but is soluble in an organic solvent and wherein said at least one film-forming polymer has an average molecular weight ranging from 5,000 to 700,000 and is selected from:

polyoxyethylenated vinyl acetate/crotonic acid copolymers;

vinyl acetate/crotonic acid (90:10) copolymer;

vinyl acetate/crotonic acid/vinyl neodecanoate terpolymers;

N-octylacrylamide/methylmethacrylate/hydroxypropyl methacrylate/acrylic acid/tert-butylaminoethyl methacrylate copolymers;

methyl vinyl ether/maleic anhydride (50:50) alternating copolymer monoesterified with butanol;

acrylic acid/ethyl acrylate/N-tertbutylacrylamide terpolymers; and polymers corresponding to the following formula:
in which:

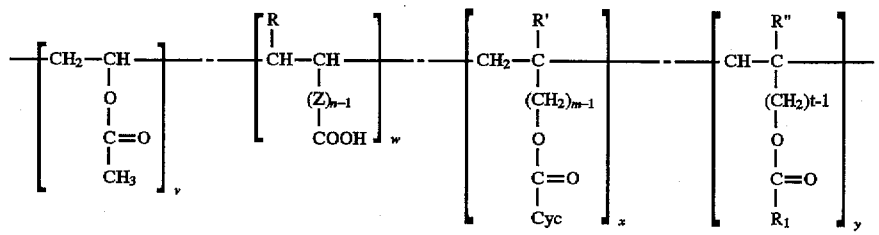

R, R' and R", which may be identical or different, represent a hydrogen atom or a methyl radical;

m, n and t are equal to 1 or 2;

$R_1$ represents a saturated or unsaturated, linear or branched alkyl radical having from 2 to 21 carbon atoms;

z represents a bivalent radical selected from:

—$CH_2$—, —$CH_2$—O—$CH_2$— and —$CH_2$—O—$(CH_2)_2$—;

Cyc represents a radical selected from:

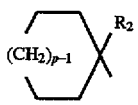

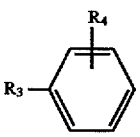

-continued

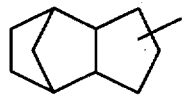

in which $R_2$ represents a hydrogen atom or a methyl radical;

$R_3$ represents a hydrogen atom or a methyl, ethyl, tert-butyl, ethoxy, butoxy or dodecyloxy radical;

$R_4$ represents a hydrogen atom, an alkyl radical having from 1 to 4 carbon atoms or an alkoxy radical having from 1 to 4 carbon atoms;

p is equal to 1 or 2;

v represents from 10 to 91% by weight, w represents from 3 to 20% by weight, x represents from 4 to 60% by weight, y represents from 0 to 40% by weight, and v+w+x+y being equal to 100%.

* * * * *

UNITED STATES PATENT AND TRADEMARK OFFICE
CERTIFICATE OF CORRECTION

Page 1 of 2

PATENT NO. : 5,683,681
DATED : November 21, 1997
INVENTOR(S) : Roland RAMIN et al.

It is certified that error appears in the above-identified patent and that said Letters Patent is hereby corrected as shown below:

Column 2, lines 48-58,

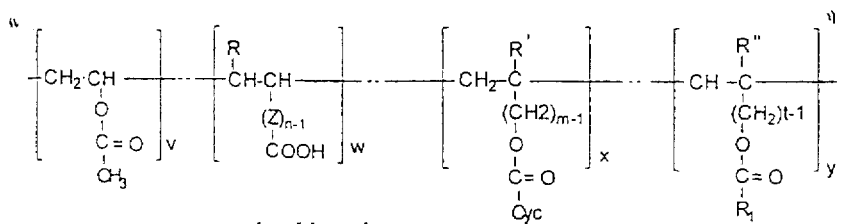

should read

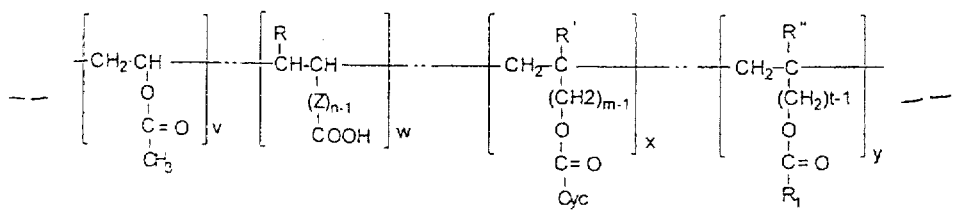

IN THE CLAIMS:

Claim 2, col. 8, line 5, "claim 1" should read --claim 14--;

Claim 2, col. 8, lines 10-20, and Claim 14, col. 9, lines 23-33,

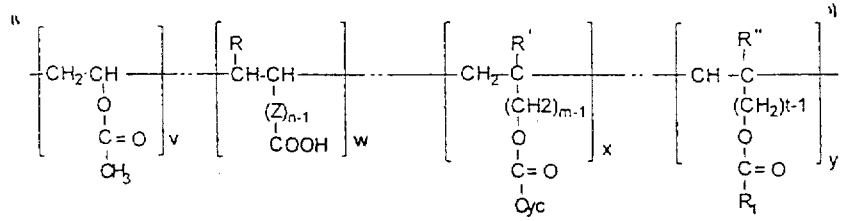

UNITED STATES PATENT AND TRADEMARK OFFICE
CERTIFICATE OF CORRECTION

PATENT NO. : 5,683,681
DATED : November 21, 1997
INVENTOR(S) : Roland RAMIN et al.

It is certified that error appears in the above-identified patent and that said Letters Patent is hereby corrected as shown below:

should read

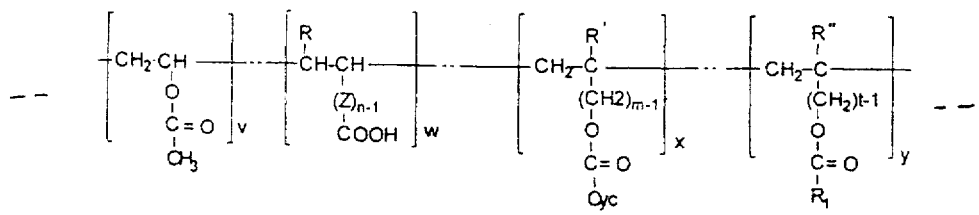

Signed and Sealed this

Twenty-seventh Day of January, 1998

Attest:

BRUCE LEHMAN

Attesting Officer

Commissioner of Patents and Trademarks